US008697433B2

(12) United States Patent
Oh et al.

(10) Patent No.: US 8,697,433 B2
(45) **Date of Patent: *Apr. 15, 2014**

(54) POLYMERASE CHAIN REACTION (PCR) MODULE AND MULTIPLE PCR SYSTEM USING THE SAME

(75) Inventors: Kwang-wook Oh, Hwaseong-si (KR); Jin-tae Kim, Hwaseong-si (KR); Kak Namkoong, Seoul (KR); Chin-sung Park, Yongin-si (KR); Yoon-kyoung Cho, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 160 days.

This patent is subject to a terminal disclaimer.

(21) Appl. No.: 12/843,552

(22) Filed: Jul. 26, 2010

(65) Prior Publication Data

US 2010/0311070 A1 Dec. 9, 2010

Related U.S. Application Data

(63) Continuation-in-part of application No. 10/890,350, filed on Jul. 13, 2004, now Pat. No. 7,767,439, and a continuation-in-part of application No. 11/080,705, filed on Mar. 15, 2005, now Pat. No. 7,799,557.

(30) Foreign Application Priority Data

Dec. 10, 2003 (KR) ........................ 10-2003-0089352
Dec. 8, 2004 (KR) ........................ 10-2004-0102738

(51) Int. Cl.

| | |
|---|---|
| *C12M 1/00* | (2006.01) |
| *C12M 1/36* | (2006.01) |
| *C12M 1/38* | (2006.01) |
| *C12M 1/34* | (2006.01) |
| *C12M 3/00* | (2006.01) |

(52) U.S. Cl.
USPC .................. 435/287.2; 435/283.1; 435/287.1; 435/288.7; 435/286.1

(58) Field of Classification Search
USPC ................................. 435/287.2, 283.1–309.4
See application file for complete search history.

(56) References Cited

U.S. PATENT DOCUMENTS

| | | | |
|---|---|---|---|
| 5,498,392 A | 3/1996 | Wilding et al. | |
| 5,538,848 A | 7/1996 | Livak et al. | |
| 5,589,136 A | 12/1996 | Northrup et al. | |
| 6,126,804 A | 10/2000 | Andresen | |
| 6,174,670 B1 | 1/2001 | Wittwer et al. | |
| 6,369,893 B1 * | 4/2002 | Christel et al. | 356/417 |
| 6,403,037 B1 | 6/2002 | Chang et al. | |

(Continued)

FOREIGN PATENT DOCUMENTS

| | | | |
|---|---|---|---|
| KR | 1020030073255 | A | 9/2003 |
| WO | 03076661 | A1 | 9/2003 |

OTHER PUBLICATIONS

European Patent Office Examination Report; Issued Jun. 11, 2007.

(Continued)

*Primary Examiner* — Nathan Bowers
*Assistant Examiner* — Lydia Edwards
(74) *Attorney, Agent, or Firm* — Cantor Colburn LLP

(57) ABSTRACT

Provided are a PCR module and a multiple PCR system using the same. More particularly, provided are a PCR module with a combined PCR thermal cycler and PCR product detector, and a multiple PCR system using the same.

20 Claims, 17 Drawing Sheets

(56) References Cited

U.S. PATENT DOCUMENTS

| | | | |
|---|---|---|---|
| 6,565,815 | B1 | 5/2003 | Chang et al. |
| 6,582,987 | B2 | 6/2003 | Jun et al. |
| 6,959,492 | B1 * | 11/2005 | Matsumoto et al. ..... 29/890.039 |
| 2002/0012910 | A1 | 1/2002 | Weiss et al. |
| 2002/0034745 | A1 | 3/2002 | McMillan et al. |
| 2002/0072054 | A1 | 6/2002 | Miles et al. |
| 2002/0114734 | A1 * | 8/2002 | Pantoliano et al. ............. 422/67 |
| 2002/0137196 | A1 | 9/2002 | Miles et al. |
| 2003/0008286 | A1 | 1/2003 | Zou et al. |
| 2003/0169799 | A1 | 9/2003 | Cho |
| 2003/0190608 | A1 | 10/2003 | Blackburn |
| 2004/0100284 | A1 * | 5/2004 | Lee et al. ...................... 324/663 |

OTHER PUBLICATIONS

Simultaneous Amplification and Detection of Specific DNA Sequences; Authors: Russell Higuchi, Gavin Dollinger, P. Sean Walsh and Robert Griffith; Bio/Technology vol. 10; Apr. 1992; pp. 413-417.

Korean Office Action for Korean patent application No. 10-2004-0102738 dated Jun. 20, 2006 with English Translation.

* cited by examiner

POLYMERASE CHAIN REACTION (PCR) MODULE AND MULTIPLE PCR SYSTEM USING THE SAME

CROSS-REFERENCE TO RELATED APPLICATIONS

This is a continuation-in-part application of U.S. patent application Ser. No. 11/080,705, filed on Mar. 15, 2005 and issued as U.S. Pat. No. 7,799,557 on Sep. 21, 2010, which in turn is a continuation-in-part application of U.S. patent application Ser. No. 10/890,350, filed on Jul. 13, 2004 and issued as U.S. Pat. No. 7,767,439 on Aug. 3, 2010, and which claims priority to Korean Patent Application Nos. 10-2003-0089352 filed on Dec. 10, 2003 and 10-2004-0102738 filed on Dec. 8, 2004 under 35 U.S.C. §119, the disclosures of which are incorporated herein in their entirety.

BACKGROUND

1. Field

The present disclosure relates to polymerase chain reaction (hereinafter, simply referred to as PCR) modules and multiple PCR systems using the same, and more particularly, to PCR modules with a combined PCR thermal cycler and PCR product detector, and multiple PCR system using the same.

2. Description of the Related Art

The science of genetic engineering originated with the discovery of restriction enzymes. Similarly, PCR technology led to an explosive development in the field of biotechnology, and thus, it may be said that the PCR technology is a contributor to the golden age of biotechnology. PCR is a technology to amplify DNA copies of specific DNA or RNA fragments in a reaction chamber. Due to a very simple principle and easy applications, the PCR technology has been extensively used in medicine, science, agriculture, veterinary medicine, food science, and environmental science, in addition to pure molecular biology, and its applications are now being extended to archeology and anthropology.

PCR is performed by repeated cycles of three steps: denaturation, annealing, and extension. In the denaturation step, a double-stranded DNA is separated into two single strands by heating at 90° C. or more. In the annealing step, two primers are each bound to the complementary opposite strands at an annealing temperature of 55 to 60° C. for 30 seconds to several minutes. In the extension step, primer extension occurs by DNA polymerase. The time required for the primer extension varies depending on the density of template DNA, the size of an amplification fragment, and an extension temperature. In the case of using Thermusaquaticus (Taq) polymerase, which is commonly used, the primer extension is performed at 72° C. for 30 seconds to several minutes.

Generally, PCR products are separated on a gel and the approximate amount of the PCR products is estimated. However, faster and more accurate quantification of PCR products is increasingly necessary. Actually, an accurate measurement of the amount of target samples in gene expression (RNA) analysis, gene copy assay (quantification of human HER2 gene in breast cancer or HIV virus burden), genotyping (knockout mouse analysis), immuno-PCR, etc. is very important.

However, conventional PCR is end-point PCR for qualitative assay of amplified DNA by gel electrophoresis, which causes many problems such as inaccurate detection of the amount of DNA. To overcome the problems of the conventional end-point PCR, a quantitative competitive (QC) PCR method was developed. The QC-PCR is based on co-amplification in the same conditions of a target and a defined amount of a competitor having similar characteristics to the target. The starting amount of the target is calculated based on the ratio of a target product to a competitor product after the co-amplification. However, the QC-PCR is very complicated in that the most suitable competitor for each PCR has to be designed, and multiple experiments at various concentrations for adjusting the optimal ratio range (at least a range of 1:10 to 10:1, 1:1 is an optimal ratio) of the target to the competitor has to be carried out. The success probability for accurate quantification is also low.

In view of these problems of the conventional PCR methods, there has been introduced a real-time PCR method in which each PCR cycle is monitored to measure PCR products during the exponential phase of PCR. At the same time, there has been developed a fluorescence detection method for quickly measuring PCR products accumulated in a tube at each PCR cycle, instead of separation on a gel. UV light analysis of ethidium bromide-containing target molecules at each cycle and detection of fluorescence with a CCD camera were first reported by Higuchi et al. in 1992. Therefore, an amplification plot showing fluorescent intensities versus cycle numbers may be obtained.

However, in a conventional real-time PCR system, all wells or chips have to be set to the same temperature conditions due to use of metal blocks such as peltier elements. Even though it may be advantageous to carry out repeated experiments using a large amount of samples at the same conditions, there are limitations on performing PCR using different samples at different temperature conditions. Also, since metal blocks such as peltier elements are used for temperature maintenance and variation, a temperature transition rate is as low as 1-3° C./sec, and thus, a considerable time for temperature transition is required, which increases the duration of PCR to more than 2 hours. In addition, the temperature accuracy of ±0.5° C. limits fast and accurate temperature adjustment, which reduces the sensitivity and specificity of PCR.

SUMMARY

Provided are polymerase chain reaction (PCR) modules in which co-amplification of different samples at different temperature conditions may be carried out and monitored in real time.

Provided are multiple PCR systems using the PCR module.

Provided are real-time PCR monitoring methods using the PCR modules or the multiple PCR systems.

Additional aspects will be set forth in part in the description which follows and, in part, will be apparent from the description, or may be learned by practice of the presented embodiments.

According to an aspect of the present invention, a PCR module includes a heater including a heater wire and a temperature sensor; a first housing for fixing the heater; a PCR tube thermally contacting with the heater and comprising a PCR chamber containing a PCR solution; a second housing fixed to the first housing, for fixing the PCR tube; and a detection unit detecting a PCR product signal.

According to an aspect of the present invention, a multiple PCR system includes the PCR module; and a host computer controlling the PCR module, wherein the PCR module and the host computer are electrically connected through a wire or wireless mode.

According to an aspect of the present invention, a multiple PCR system includes the PCR module; and a host computer controlling the PCR module, wherein the PCR module includes a computing unit and the computing unit of the PCR module and the host computer are electrically connected through a wire or wireless network.

According to an aspect of the present invention, a real-time PCR monitoring method includes (a) loading a PCR solution in a PCR chamber of a PCR tube received in each of one or more PCR modules; (b) performing PCR independently in the PCR chamber of the PCR tube of each PCR module having an independently determined temperature condition; (c) detecting a PCR product signal based on PCR performed in each PCR module; and (d) displaying data about the PCR product signal of each PCR module.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1A:
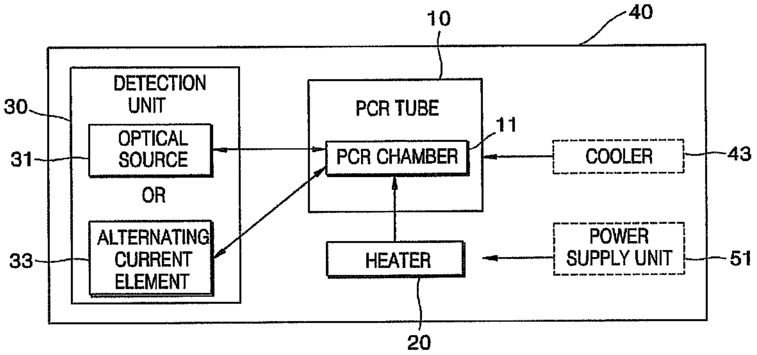
FIG. 1A is a schematic block diagram of a polymerase chain reaction (PCR) module according to an embodiment of the present invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

FIG. 1A is a schematic block diagram of a polymerase chain reaction (PCR) module according to an embodiment of the present invention. Referring to FIG. 1A, a PCR module 40 according to the present embodiment includes a PCR tube 10 having a PCR solution-containing PCR chamber 11 and a detection unit 30 for detecting a PCR product signal based on the amount of a PCR product of the PCR solution contained in the PCR chamber 11 of the PCR tube 10.

Here, the "the PCR tube 10" indicates a disposable or reusable device that is detachable from the PCR module 40, generally a microchip-type PCR tube. For example, the PCR tube 10 is mainly made of silicon. Therefore, heat generated by a heater 20 may be rapidly transferred, and thus, a temperature transition rate may be remarkably enhanced, relative to a conventional technology. Furthermore, PCR may be performed for smaller amounts of unconcentrated samples, unlike a conventional technology. For example, the PCR chamber 11 has a capacity of several tens microliters or less. If the capacity of the PCR chamber 11 exceeds several tens microliters, the content of a sample increases, thereby remarkably retarding PCR and increasing the size of the PCR tube 10. In this respect, the PCR chamber 11 with the capacity of more than several tens micrometers is not appropriate with a view to the capacity of the entire system.

The PCR tube 10 includes the PCR chamber 11 as described above. The PCR chamber 11 contains a PCR solution. The PCR solution may be controlled to an appropriate temperature range by feedbacking the temperature of the PCR solution accurately measured by the temperature sensor. An impedance measurement sensor is used to measure impedance in a PCR solution as a PCR product signal using a chip (10 of FIG. 7) for monitoring the impedance in real time and the detection unit 30 including an alternating power element, unlike the temperature sensor measuring the temperature of the PCR solution.

Figure 8A:
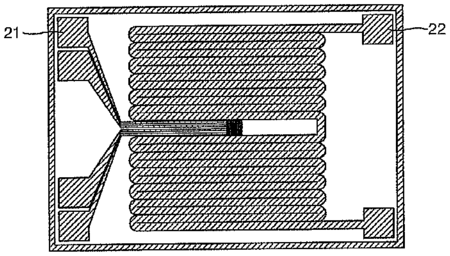
FIG. 8A is a rear view of a heater provided with a temperature sensor of FIG. 6.

The heater 20 contained in the PCR module 40 is separately disposed from the PCR tube 10 and contacts with a lower surface of the PCR tube 10 to apply heat to the PCR tube 10. FIG. 8A is a rear view of the heater 20 including a temperature sensor 21 and a heater wire. The heater 20 is provided with a temperature sensor 21 and a heat wire 22 on its lower surface to adjust on/off of the heater 20 so that the PCR tube 10 is maintained at an appropriate temperature.

The temperature sensor 21 is positioned on a central portion of the heater 20, and detects a temperature change. A resistance change of the temperature sensor 21 due to the temperature change may be converted into a voltage, and then may be transmitted to a computing unit through four terminals connected to the temperature sensor 21. In this case, a four-point measuring method, or a three-point measuring method may be used. In the four-point measuring method, central two terminals of the four terminals are used to measure a voltage while allowing a predetermined current to flow through external two terminals of the four terminals. In the three-point measuring method, a bridge is formed by using only any three terminals of the four terminals.

The heat wire 22 may have a winding shape. In addition, on/off of the heat wire 22 may be controlled according to a temperature that is measured by the temperature sensor 21. For example, the heater 20 is a microplate heater.

The temperature sensor 21 and the heat wire 22 may be formed on the lower surface of the heater 20, and may be formed of the same material.

As such, since the heater 20 and the PCR tube 10 are separately formed, only the PCR tube 10 may be replaced, and thus temperature calibration of the heater 20 does not have to be repeatedly performed, thereby improving the durability and lifetime of the heater 20.

Figure 8B:
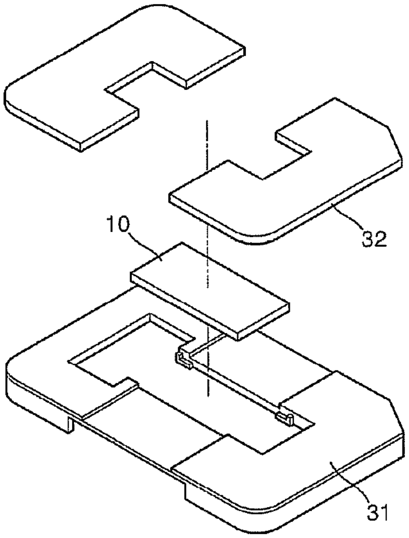
FIGS. 8B and 8C is a perspective view of a second housing to which the PCR tube is fixed, according to an embodiment of the present invention.
Figure 8C:
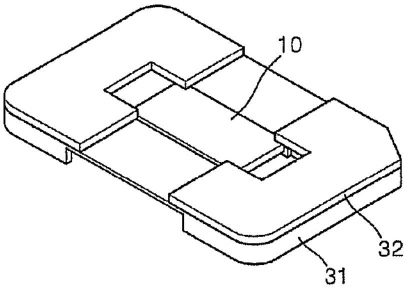

Since the heater 20 and the PCR tube 10 are separately formed, a separate housing is required in order to fix the heater 20 and the PCR tube 10. FIGS. 8B and 8C are a perspective view of a second housing to which the PCR tube 10 is fixed, according to an embodiment of the present invention. The second housing fixes the PCR tube 10 by positioning the PCR tube 10 on a central portion of a base 31 and then covering the PCR tube 10 with two covers 32. The base 31 and the covers 32 engage with each other to be fixed. A handling groove may be formed in a lateral surface of the second housing so as to prevent the second housing from being damaged due to slipping. A tapered structure may be formed at any one corner of the second housing so as to provide directivity.

Figure 8D:
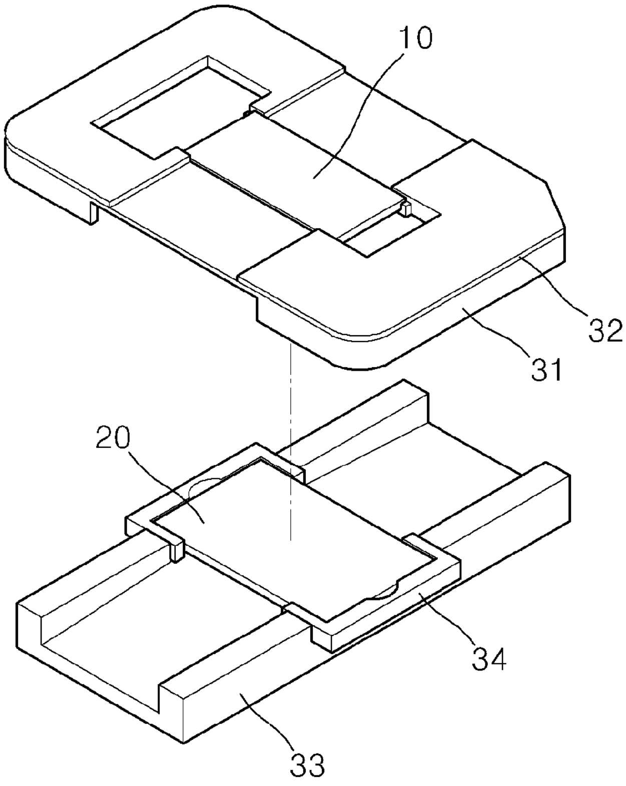
FIG. 8D is a perspective view of a first housing including a heater, according to an embodiment of the present invention.
Figure 8E:
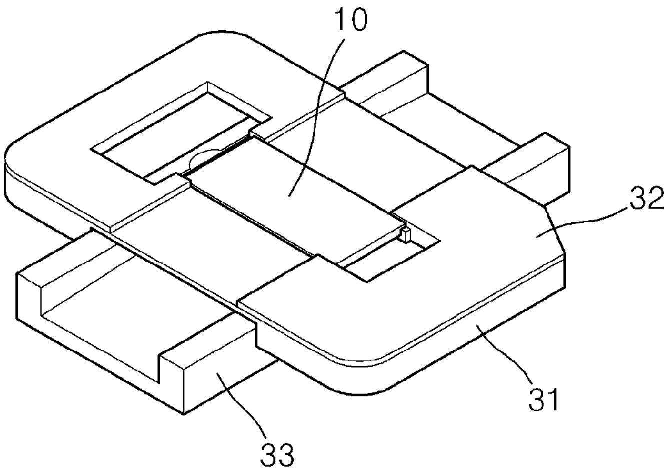
FIG. 8E illustrates a case where the first housing and the second housing are coupled, according to an embodiment of the present invention.

Likewise, the heater 20 is also fixed to a first housing. As shown in FIG. 8D, the first housing fixes the heater 20 which is inserted into a clamp 34 positioned on a base 33. FIG. 8E illustrates a case where the first housing and the second housing are coupled, according to an embodiment of the present invention. When the PCR tube 10 fixed to the second housing is positioned on the first housing to which the heater 20 is fixed, the first housing and the second housing engage with each other to be coupled to each other. As a result, the lower surface of the PCR tube 10 contacts an upper surface of the heater 20 to transfer heat to the heater 20.

The PCR tube 10 and the heater 20 may directly contact each other. Alternatively, a heat-transfer facilitating layer may be further provided between the PCR tube 10 and the heater 20, in order to uniformly transfer heat. A graphite sheet may be used as the heat-transfer facilitating layer.

After the second housing including the PCR tube 10 is coupled to the first housing including the heater 20, a sealing member may be positioned on the second housing. The sealing member may be fixed to the second housing by a fixer so as to seal an entrance of the PCR tube 10.

The PCR module 40 may further include a power supply unit 51 so that a fixed voltage is applied to the heater 20. The heater 20 may apply a uniform temperature to the PCR tube 10 for stable thermal transfer by electric power supplied from the power supply unit 51. However, in some cases, the power supply unit 51 may apply an electric power to the heater 20, together with another power supply unit connected to another device.

For example, the PCR module 40 may further include a cooler 43, in addition to the heater 20, so that the PCR solution in the PCR tube 10 is set to a desired temperature. That is, the cooler 43 is used to perform thermal circulation cycles by rapid temperature transition. As the cooler 43, there may be used a cooling fan for cooling an ambient air of the PCR module 40 to adjust the temperature of the PCR solution or a peltier device attached to the PCR tube 10 or the module 40 to adjust the temperature of the PCR solution. A water cooler may also be used. If necessary, an airguide or a heatsink may be installed to enhance thermal conductivity.

The detection unit 30 of the PCR module 40 includes an optical source 31 or an alternating power element 33 and is used to detect a PCR product signal based on the amount of a PCR product. The principle and construction of the detection unit 30 will be described later.

Figure 1B:
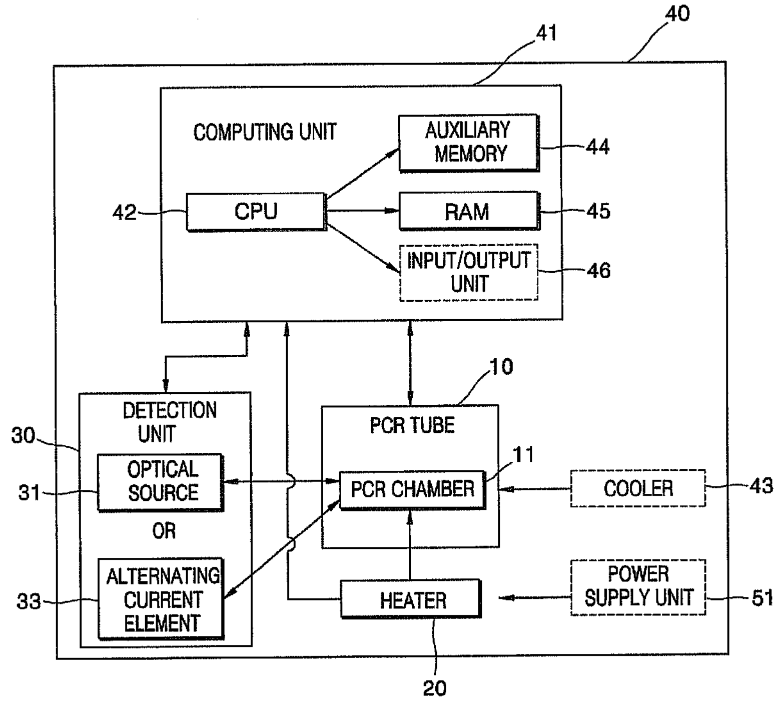
FIG. 1B is a schematic block diagram of a PCR module including a computing unit, according to an embodiment of the present invention.

FIG. 1B is a schematic block diagram of a PCR module 40 including a computing unit 41, according to an embodiment of the present invention. The PCR module 40 according to the present embodiment shown in FIG. 1A is operated in a passive mode. However, when the computing unit 41 is added to the PCR module 40, the whole processes of PCR may be automatically performed in a predetermined sequence or under real-time control. The computing unit 41 includes a central processing unit (CPU) 42, also known as microprocessor, an auxiliary memory 44, and a random access memory (RAM) 45 and controls a PCR procedure according to a determined program. The computing unit 41 independently performs real-time control of the detection unit 30, the PCR tube 10, the heater 20, the cooler 43, the power supply unit 51, and the like, through a data communication unit (not shown). The computing unit 41 performs appropriate computation based on data received from attachment sensors or the data communication unit and then performs a predetermined operation according to a determined program or an optional parameter value defined by a user. For example, the computing unit 41 may appropriately adjust the temperature of the PCR chamber 11 during PCR or determine the operating or suspending of the cooler 43 and the detection time interval of the detection unit 30. The computing unit 41 may further include a separate input/output unit 46 so that the PCR module 40 may be independently operated.

The computing unit 41 is operated according to a software program stored in the auxiliary memory 44. The auxiliary memory 44 is not particularly limited provided that it is that commonly used in the computation related field. For example, there may be used one or more selected from a hard disk, a floppy disk, an optical disk (CD, DVD, MD, etc.), a magnetic disk, and a flash memory card. CD used as the auxiliary memory 44 is used through a CD-ROM drive and a flash memory card used as the auxiliary memory 44 is used through a memory reader. The flash memory card is most appropriate because of its small size, easy use, and low power consumption. The flash memory card may be optionally selected from those known in the pertinent art. All types of flash memory cards such as Compact Flash (CF), Secure Digital (SD), Micro Drive (MD), memory stick, and eXtreme Digital (XD) may be used.

For example, a PCR software program for operating the computing unit 41 is stored in the auxiliary memory 44 as described above and used if necessary. The auxiliary memory 44 also stores various data about user-defined parameters for PCR, i.e., PCR temperature and cycle number. A separate power supply unit may be connected to the computing unit 41.

Figure 2:
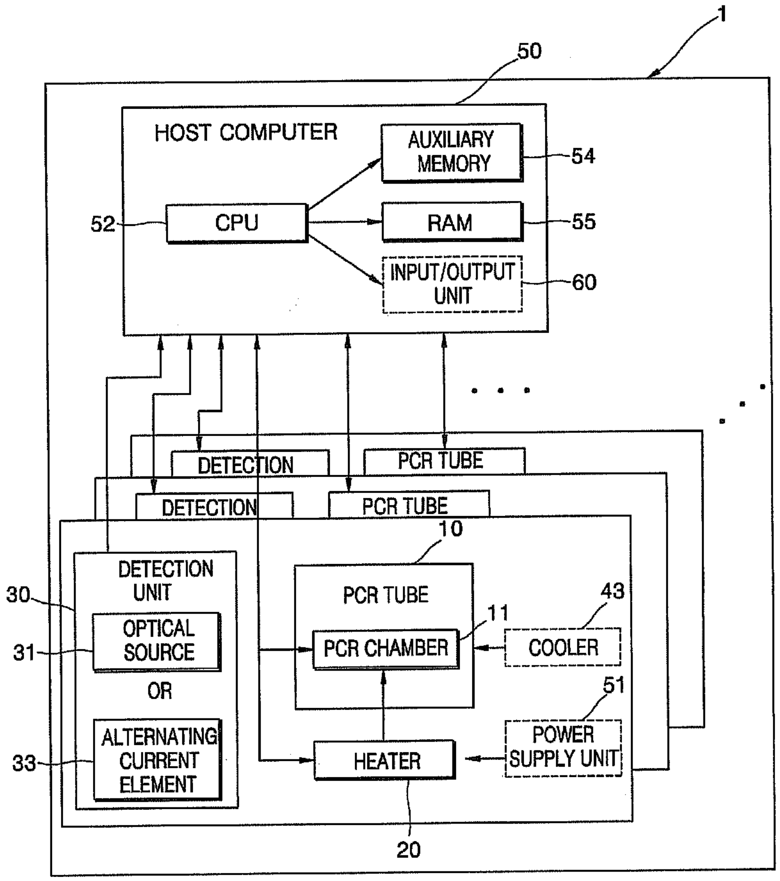
FIG. 2 is a schematic block diagram of a multiple PCR system including a host computer, according to an embodiment of the present invention.
Figure 3:
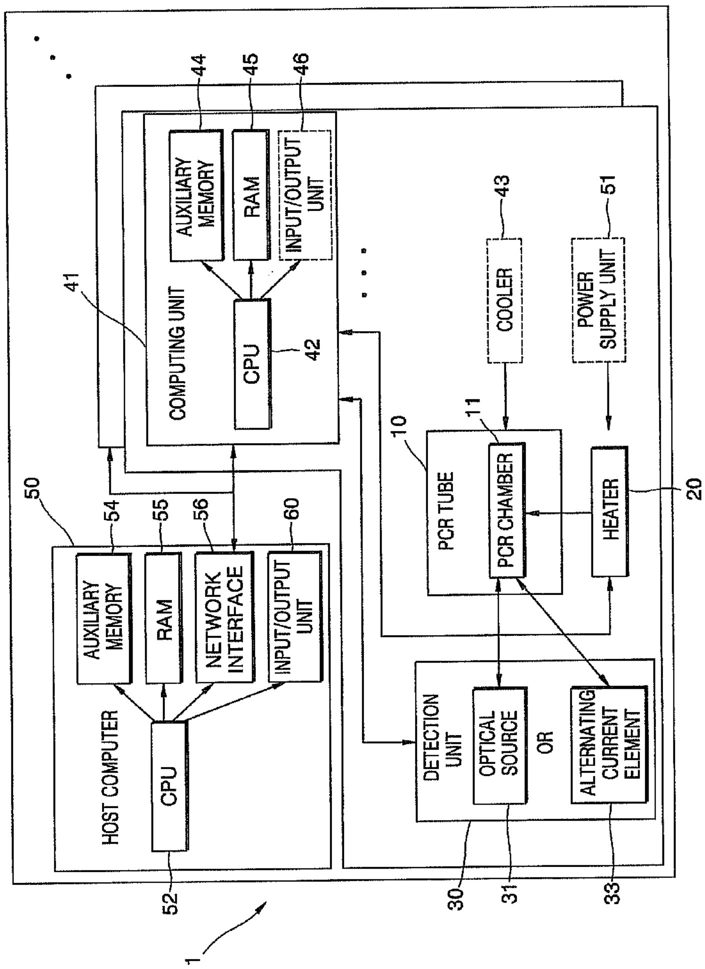
FIG. 3 is a schematic block diagram of a multiple PCR system including a host computer and a PCR module, according to an embodiment of the present invention.

FIGS. 2 and 3 illustrate schematic block diagrams of multiple PCR systems 1 in which the above-described PCR module 40, i.e., the PCR module 40 with or without the computing unit 41 is connected to a host computer 50.

The multiple PCR systems 1 according to the present embodiment include one or more PCR modules 40 and are used for PCR for different samples at different PCR conditions. That is, the multiple PCR systems 1 are used to independently and simultaneously perform the real-time control of several PCR procedures, thereby enhancing PCR efficiency.

With respect to a multiple PCR system 1 shown in FIG. 2, no computing units are not contained in one or more PCR modules 40. Here, the multiple PCR system 1 has a connection structure of the one or more PCR modules 40 to a data communication unit (not shown) of a host computer 50. That is, each of the PCR modules 40 includes a detection unit 30, a PCR tube 10, a heater 20, and the like, and these constitutional elements are controlled by received or transmitted data through data communication with the host computer 50. The PCR modules 40 are detachably installed in the multiple PCR system 1 so that they are connected to the host computer 50 if necessary. There is no particular limitation on the number of the PCR modules 40. For example, the PCR modules 40 are composed of 2 to 24 numbers. If the number of the PCR modules 40 is too high, the host computer 50 may not appropriately control the PCR modules 40. In this regard, it is appropriate to adjust the number of the PCR modules 40 according to the processing capability of the host computer 50.

The host computer 50 includes a CPU 52, an auxiliary memory 54, a RAM 55, and an input/output unit 60 and controls a PCR procedure according to a software program stored in the auxiliary memory 54. As described above, the auxiliary memory 54 may be one or more selected from a hard disk, an optical disk, a floppy disk, and a flash memory card. The software program stored in the auxiliary memory 54 has an additional management function for independently controlling the PCR modules 40, unlike the above-described computing unit 41 that has only a necessary function for controlling constitutional elements of the module 40. That is, the software program stored in the auxiliary memory 54 may independently control the detection unit 30, the heater 20, and the PCR tube 10 contained in each of the PCR modules 40 so that PCR for different samples may be controlled at the different conditions. Furthermore, parameter values optionally defined by a user are stored in the auxiliary memory 54.

The host computer 50 includes the input/output unit 60, unlike the computing unit 41. The input/output unit 60 serves to input user-defined parameter values or display in real time various data received from the PCR modules 40. According to the input or displayed data, a PCR procedure may be appropriately controlled by changing or modifying in real time the user-defined parameter values. For example, a liquid crystal display is used as a display portion of the input/output unit 60 with a view to power consumption or dimension. In this case, it is more appropriate to install a touch screen type input element on the display portion. Of course, a common keyboard, CRT, etc. may also be used.

The host computer 50 communicates with the PCR modules 40 via a data communication unit (not shown) through a wire or wireless mode. Common wire or wireless modes known in the pertinent art may be unlimitedly used. For example, a serial port such as RS-232C, a parallel port, a USB port, a 1394 port, etc. may be used for communication through the wire mode. It is appropriate to use a USB port considering extendability. A radio frequency (RF) mode may be used for wireless communication.

In particular, the detection unit 30 in each of the PCR modules 40 detects a PCR product signal in the PCR tube 10 and transmits the detected signal to the host computer 50 through a wire or wireless mode. For example, the PCR product signal may be a fluorescence signal emitted from the PCR chamber 11 disposed in the PCR tube 10. The detection unit 30 acts as a fluorescence detector that detects a fluorescence signal and transmits the detected signal to the host computer 50. For this, the detection unit 30 includes an optical source 31 for applying light to the PCR solution. When light from the optical source 31 is applied to the PCR solution, the fluorescence emitted from the PCR solution is concentrated on a lens (not shown) and recorded after passing through a filter.

The PCR product signal may also be an electrical signal. In this case, the detection unit 30 includes a sensor (not shown) for sensing an electrical signal. The sensor is disposed in the PCR tube 10. The sensor detects a PCR product signal emitted when an alternating current is applied to the PCR solution in the PCR chamber 11 disposed in the PCR tube 10 and transmits the detected signal to the host computer 50. The received data is displayed on the display portion of the input/output unit 60 to be viewed by a user. For this, the detection unit 30 includes an alternating power element 33.

The host computer 50 may include a separate power supply unit (not shown) for stable power supply. The power supply unit may simultaneously perform power supply to the constitutional elements of the PCR modules 40. That is, the host computer 50 and the PCR modules 40 may receive an electric power from individual power supply units or a single common power supply unit. This is also applied to the detection unit 30 and the heater 20 contained in each of the PCR modules 40.

FIG. 3 illustrates a multiple PCR system 1 in which one or more PCR modules 40 include respective computing units 41. That is, in the multiple PCR system 1 shown in FIG. 3, the computing units 41 contained in the PCR modules 40 perform a necessary function for substantially controlling a PCR procedure. A host computer 50 serves only to manage the computing units 41 by data communication with the computing units 41. The multiple PCR system 1 includes the respective computing units 41 in the PCR modules 40, and thus, the PCR modules 40 are independently controlled. Therefore, the multiple PCR system 1 has extendability regardless of the processing capability of the host computer 50, thereby removing a limitation of the number of the detachable PCR modules 40. In this respect, a considerable number of the PCR modules 40 may be mounted in the multiple PCR system 1 within the permissible capacity of the multiple PCR system 1. In particular, in a case where the host computer 50 and the PCR modules 40 are connected through a wire or wireless mode, there is no limitation on extendability, thereby ensuring almost unlimited extendability.

As described above, the host computer 50 and the computing units 41 have respective auxiliary memories 54 and 44. The auxiliary memories 54 and 44 store software programs for PCR control and the software programs execute their functions. In particular, the software programs may be connected through wire or wireless network such as a pier-pier network or a server-client network. For example, a LAN transmission technology using a common network interface card or hub may be used through a wire or wireless mode. Through such a connection system, the PCR modules 40 are controlled remotely by the host computer 50 through real-time data communication, thereby independently controlling the PCR modules 40. As described above, the computing units 41 may independently control constitutional elements in the respective PCR modules 40.

In particular, in the multiple PCR system 1 shown in FIG. 3, even though data detected by the detection unit 30 may be directly transmitted to the host computer 50, in a case where the detection unit 30 is controlled by each of the computing units 41, it is appropriate that detected data are transmitted to the computing units 41 and then to the host computer 50. The detection mechanism of the detection unit 30 is as described above.

Figure 4:
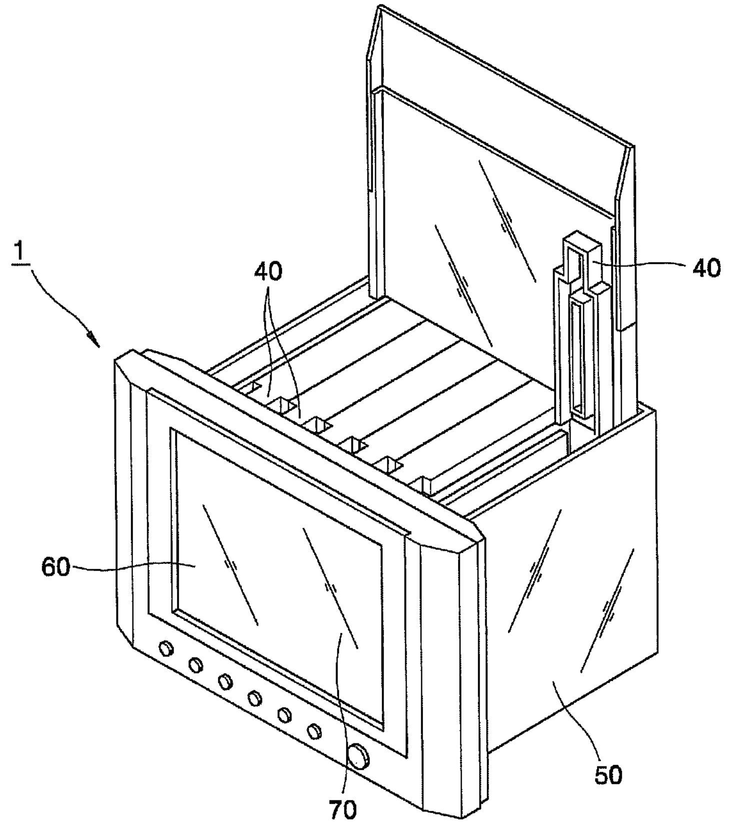
FIG. 4 is a schematic perspective view of a multiple PCR system according to an embodiment of the present invention.

FIG. 4 is a schematic perspective view of a multiple PCR system 1 according to an embodiment of the present invention. Referring to FIG. 4, the multiple PCR system 1 includes a microchip-type PCR tube (not shown) having a PCR solution-containing PCR chamber (not shown), a heater (not shown) for applying heat to the PCR chamber of the PCR tube, and a detection unit (not shown) for detecting a PCR product signal based on the amount of the PCR product in the PCR solution, a plurality of modules 40, a host computer 50 electrically connected to the modules 40, a display unit 60 for displaying data received from the modules 40, and an input unit 70 that permits a user to input a signal. As used herein, the modules 40 are composed of six numbers and are detachably assembled. The temperature of the PCR chamber of the PCR tube received in each of the modules 40 is independently adjusted by a computing unit (not shown) of each of the modules 40 or the host computer 50.

Figure 5:
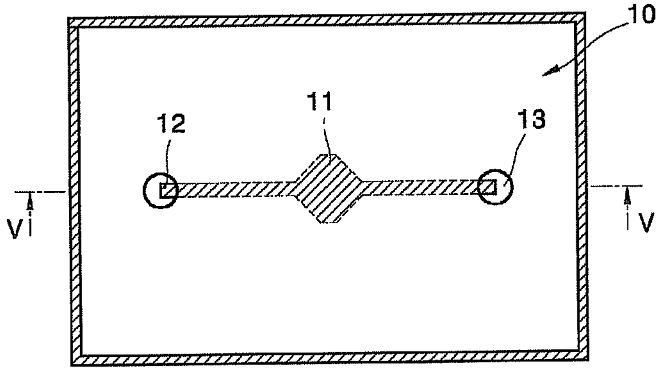
FIG. 5 is a plan view of a microchip-type PCR tube installed in a multiple PCR system when a detection unit of FIG. 1 includes an optical source.
Figure 6:
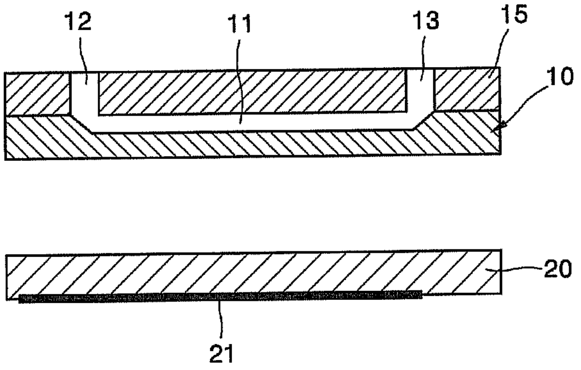
FIG. 6 is a sectional view taken along line V-V of FIG. 5.

FIG. 5 is a plan view of a microchip-type PCR tube 10 in a PCR module according to an embodiment of the present invention and FIG. 6 is a sectional view taken along line V-V of FIG. 5. Referring to FIGS. 5 and 6, the microchip-type PCR tube 10 is made of silicon and is formed with a PCR chamber 11 containing a PCR solution. The PCR chamber 11 has a sample inlet 12 for injection of the PCR solution and a sample outlet 13 for releasing of the PCR solution. A glass 15 is disposed on the PCR tube 10 made of silicon so that a detection unit (not shown) may detect a fluorescence signal emitted from the PCR product. A heater 20 is separately disposed from the PCR tube 10 and contacts with a lower surface of the PCR tube 10 to apply heat to the PCR tube 10.

A real-time PCR monitoring method using the multiple PCR system 1 according to an embodiment of the present invention in which a PCR product signal is a fluorescence signal emitted from the PCR chamber 11 will now be described in detail with reference to FIG. 3. First, a touch screen type monitor that acts as the input/output 60 of the host computer 50 receives PCR conditions, the power of an optical system, and signal measurement conditions, as input values. The input values are transmitted to the computing unit 41 of each of the modules 40, specifically, a microprocessor. The computing unit 41 permits the PCR tube 10 to have a predetermined temperature condition based on the temperature condition of the PCR tube 10 feedbacked from a temperature sensor (not shown) installed in the PCR tube 10. The computing unit 41 also determines the operating and suspending time of the optical system of the detection unit 30 so that an optical signal may n be measured in real time according to the measurement conditions. As described above, the computing unit 41 of each of the modules 40 also independently controls constitutional elements of each of the modules 40 and the host computer 50 controls the modules 40 in real time. When the computing unit 41 is not contained in the modules 40, the host computer 50 independently controls the constitutional elements in the modules 40, as described above.

A real-time PCR monitoring method using a multiple PCR system in which a PCR product signal according to another embodiment of the present invention is a signal corresponding to impedance measured from a PCR product will now be described with reference to FIG. 3. This embodiment is different from the above-described embodiment in that the detection unit 30 of each of the modules 40 includes the electrical signal, i.e., impedance measured in the PCR solution when an alternating current is applied to the PCR solution in the PCR chamber 11. In this embodiment, first, a touch screen type monitor that acts as the input/output unit 60 of the host computer 50 receives PCR conditions, the magnitude and frequency of an alternating voltage for impedance measurement as input values. These input values are transmitted to the computing unit 41 of each of the modules 40. The computing unit 41 permits the PCR tube 10 to have a predetermined temperature based on the temperature condition of the PCR tube 10 feedbacked from a signal processing circuit of the PCR tube 10. The computing unit 41 also determines the magnitude and frequency of an alternating voltage of the detection unit 30 so that impedance may be measured in real time according to the determined conditions. As described above, the computing unit 41 of each of the modules 40 also independently controls the constitutional elements of each of the modules 40 and the host computer independently controls these modules 40. When the computing unit 41 is not contained in the modules 40, the host computer 50 independently controls the constitutional elements in the modules 40.

Figure 7:
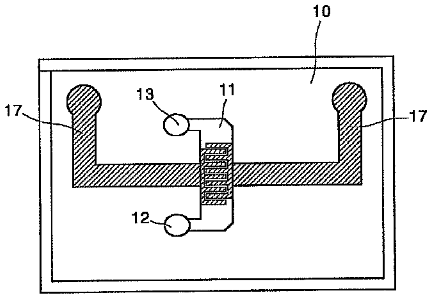
FIG. 7 is a plan view of a microchip-type PCR tube when a detection unit of FIG. 1 includes an alternating power element for impedance measurement.

FIG. 7 is a plan view of a microchip-type PCR tube 10 when a detection unit includes an alternating power unit for impedance measurement and FIG. **8*a* is a rear view of the heater 20 including the temperature sensor 21 and the heater wire 22. Referring to FIGS. 7 and 8*a*, interdigitated electrodes 17 are disposed in a PCR chamber 11. Impedance measurement is performed while an alternating current is applied to a PCR mixture, i.e., a PCR solution. A micro-heat wire 22 and a temperature sensor 21** made of a thin metal foil enables temperature control on a chip.

Hereinafter, one or more embodiments of the present invention will be described in detail with reference to the following examples. However, these examples are not intended to limit the purpose and scope of the one or more embodiments of the present invention.

EXAMPLE 1

Preparation of PCR Solution

To minimize difference between PCR experiments, other reagents except DNA samples were mixed to prepare a two-fold concentrated master mixture. Then, the master mixture was mixed with the DNA samples (1:1, by volume) to obtain a PCR solution.

The composition of the master mixture is as follows:

| | |
|---|---|
| PCR buffer | 1.0 μl |
| Distilled water | 1.04 μl |
| 10 mM dNTPs | 0.1 μl |
| 20 μM of each primer mixture | 0.2 μl |
| Enzyme mixture | 0.16 μl |

EXAMPLE 2

PCR on Microchips

To investigate the effect of a thermal transfer rate and a temperature ramping rate on PCR, PCR was carried out on micro PCR chips with the dimension of 7.5 mm×15.0 mm×1.0 mm. The micro PCR chips were made of silicon and had fast thermal transfer in reactants, and so on due to several hundreds times faster thermal conductivity than conventional PCR tubes, a fast temperature ramping rate, and maximal thermal transfer due to use of a trace of DNA samples. The micro PCR chips were fixed to the second housing illustrated in FIG. 8B.

1 μl of the PCR solution of Example 1 was loaded in each of the micro PCR chips, and a PCR cycle of 92° C. for 1 second and 63° C. for 15 seconds was then repeated for 40 times. The experimental resultants were quantified using Labchip (Agilent) and amplification was identified on a 2% TAE agarose gel.

Figure 9:
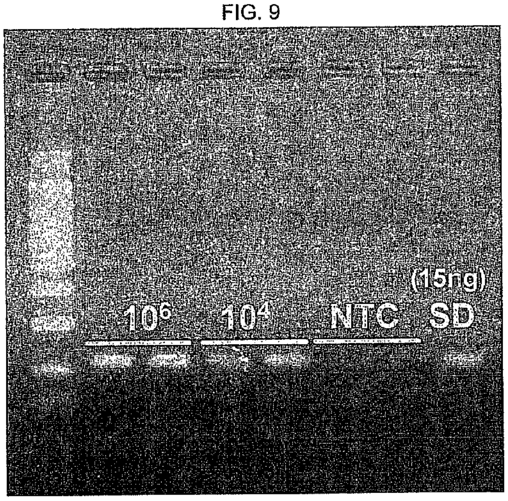
FIG. 9 illustrates an electrophoretic result on a 2% TAE agarose gel after two-stage PCR in a microchip-type PCR tube.

FIG. 9 shows electrophoretic results on a 2% TAE agarose gel after the amplification. Here, $10^6$ and $10^4$ indicate the copy numbers of a HBV template, NTC (no template control) is a negative control for PCR, and SD (standard) is a positive control for PCR.

Figure 10A:
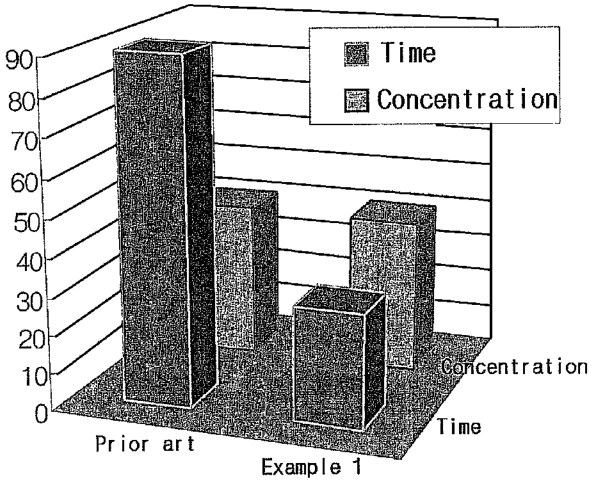
FIG. 10A is a comparative view that illustrates the duration of PCR required for obtaining almost the same DNA concentration in an embodiment of the present invention and a typical technology.
Figure 10B:
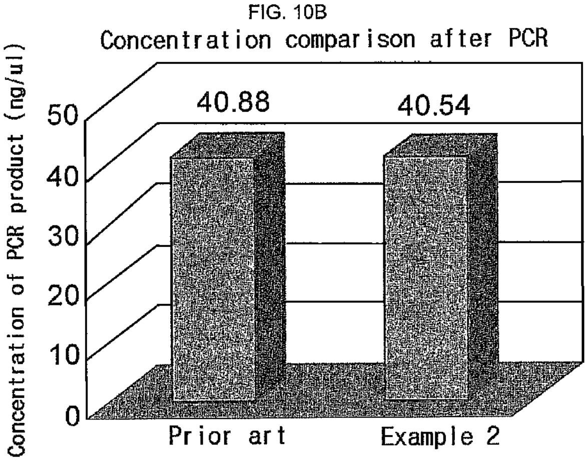
FIG. 10B is an enlarged view that illustrates only the DNA concentration of FIG. 10A.

FIGS. 10A and 10B are comparative views that illustrate the concentrations of PCR products with respect to the time required for PCR in a micro PCR chip according to an embodiment of the present invention and in a typical PCR tube (MJ research, USA). Referring to FIGS. 10A and 10B, a time required for obtaining 40.54 ng/μl of a PCR product on a micro PCR chip according to the present embodiment was only 28 minutes. This is in contrast to 90 minutes required for obtaining 40.88 ng/μl of a PCR product using a conventional PCR tube. That is, a time required for obtaining the same concentration of a PCR product using the PCR technology according to the present embodiment was only about one-third of that of using a conventional PCR tube.

Figure 11A:
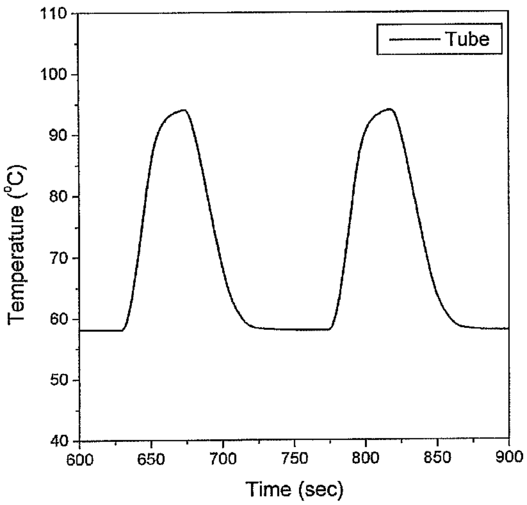
FIG. 11A is a graph that illustrates a temperature profile of a typical PCR system.
Figure 11B:
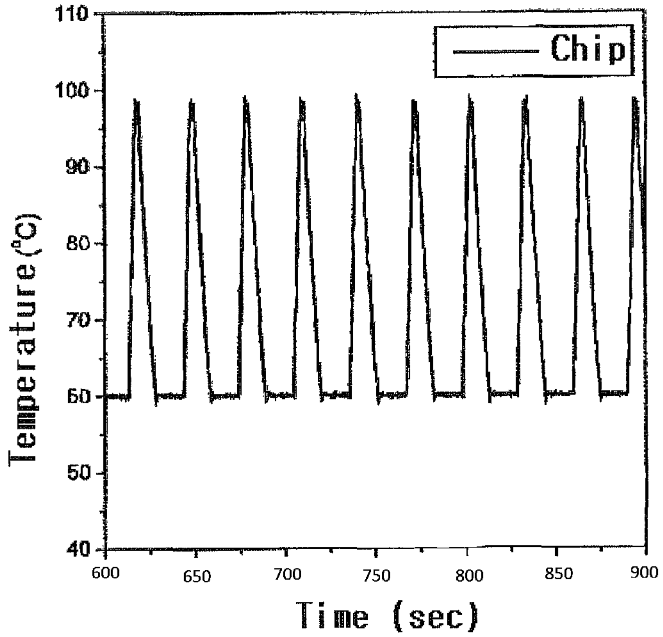
FIG. 11B is a graph that illustrates a temperature profile of a real-time PCR monitoring apparatus, according to an embodiment of the present invention.

FIG. 11A is a graph that illustrates a temperature profile for a conventional PCR tube and FIG. 11B is a graph that illustrates a temperature profile for an apparatus according to an embodiment of the present invention.

EXAMPLE 3

Real-Time PCR Experiments Using Multiple PCR System Based on Signal Corresponding to Impedance Measured in PCR Product In this Example, a signal emitted from a PCR solution (Promega) was measured in real time using the following multiple PCR system 1 as shown in FIG. 3.

Specifications of a host computer 50 and a computing unit 41 were as follows:

I. Host Computer

Industrial embedded board (manufactured by Transmeta Co., Ltd., model: AAEON Gene 6330) was used.

The GENE-6330 is thinnest board in the AAEON Sub-Compact Board series. It has a Mini-PCI slot, an onboard SMI 712 LynxEM+ graphic chip provides TFT and DSTN panel support and comes with one 10/100 Mbps Ethernet connector, four USB ports and a CompactFlash slot, offering great connectivity. Functional flexibility is enhanced through the choice of either a Type II PCMCIA and Type III Mini PCI slot.

Auxiliary memory: 2.5 inch 30 GB HDD (manufactured by Hitachi Co., Ltd.)

Network interface: RTL 8139DL, 10/100Base-T RJ-45

Input unit: 15.1 inch touch screen (manufactured by 3M Co., Ltd.)

Output unit: 15.1 inch LCD monitor (manufactured by BOE Hydis Co., Ltd.)

Operating System: MS Windows 2000 professional

II. Computing Unit

The computing unit used C8051 F061 (manufactured by Silicon Laboratories Co., Ltd.)

The Silicon Laboratories, Inc. C8051 F061 is a 25 MIPS Mixed-Signal 8051 with 24 I/O Lines, 5 Timers, Watchdog Timer, PCA, SPI, SMBus, I2C, 2 UARTS, CAN 2.0B, 2 Channel (16-bit) ND, 8 Channel (10-bit) A/D, 2 Channel (12-bit) D/A, 3 Analog Comparators, On-Chip Temperature Sensor, 64K Byte In-System Programmable FLASH, 256 Bytes RAM, 4K Bytes XRAM.

The host computer 50 and the computing unit 41 were connected through a hub over the Ethernet wire. A power supply unit installed at the host computer 50 supplied an electric power to the PCR modules 40 each including the computing unit 41. Further, the ambient temperature of the PCR modules 40 each including the PCR tube 10 was cooled by the cooler 43.

A microplate heater provided with the temperature sensor 21 and the heat wire 22 was used as the heater 20. The heater 20 was fixed to the first housing, as shown in FIG. 8D. The detection unit 30 including the alternating power unit 33 was used.

To minimize difference between PCR experiments, the PCR solution was prepared as follows: other reagents except DNA samples were mixed to prepare a two-fold concentrated master mixture and then the master mixture was mixed with the DNA samples (1:1, by volume) to obtain the PCR solution.

The composition of the master mixture is presented in Table 1 below.

TABLE 1

| Composition | | Content |
|---|---|---|
| PCR buffer | Tris HCl | 10 mM |
| | KCl | 50 mM |
| | Triton X-100 | 0.10% |
| dNTP | dATP | 200 μM |
| | dCTP | 200 μM |
| | dGTP | 200 μM |
| | dUTP (dTTP) | 200 μM |
| Primer | Upstream | 1,000 nM |
| | Downstream | 1,000 nM |
| Taq polymerase | | 0.025 U/μl |
| $MgCl_2$ | | 1.5 mM |

The temperature and duration conditions for PCR were the same as those used in conventional PCR tubes as follows: 1 cycle of 50° C. for 120 seconds and 91° C. for 180 seconds; 1 cycle of 92° C. for 1 second and 63° C. for 180 seconds; 44 cycles of 92° C. for 1 second and 63° C. for 15 seconds; and 1 cycle of 63° C. for 180 seconds.

To measure impedance values, first, 1 μl of the PCR solution as prepared previously was loaded in each of micro PCR chips via a sample inlet as shown in FIGS. 7 and 8. After the micro PCR chips were received in modules, real-time impedance values were measured under an alternating voltage of 100 mV at 100 KHz.

Figure 12A:
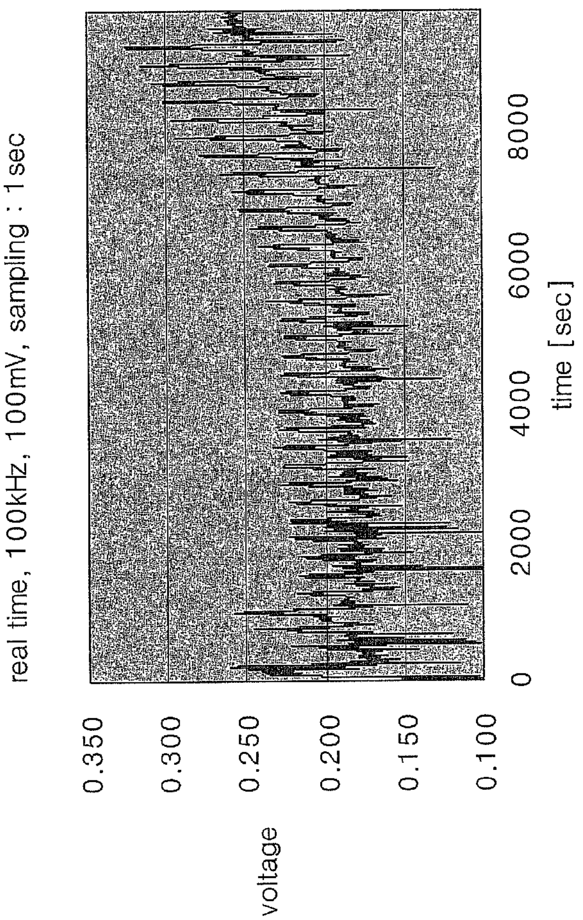
FIG. 12A is a view that illustrates real-time impedance values.
Figure 12B:
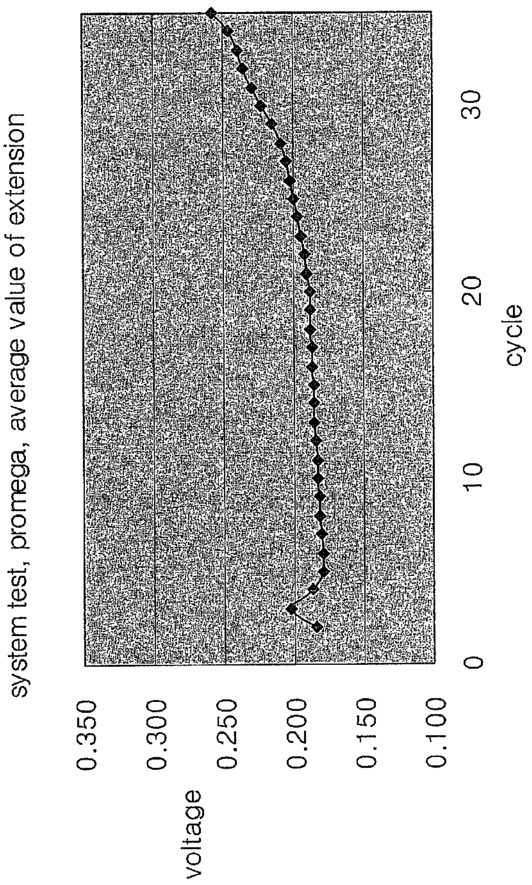
FIG. 12B is a graph that illustrates impedance values during extension versus the number of PCR cycles.

FIG. 12A shows the real-time impedance values and FIG. 12B is a graph that illustrates impedance values during extension versus the number of PCR cycles. As seen from FIGS. 12A and 12B, PCR products increased with time, and impedance increased from after about 28 cycles.

EXAMPLE 4

Real-Time Measurement and Visualization of Optical Signals

Two-stage thermal cycling for the PCR solution of Example 1 was performed according to the PCR conditions presented in Table 2 below. The same apparatus as in Example 1 was used as the multiple PCR system 1 except that the detection unit 30 including the optical source 31 was used for signal detection.

TABLE 2

| Stage | Section | Temperature (° C.) | Duration (sec.) | Cycles |
|---|---|---|---|---|
| Stage 1 | Initial UNG incubation | 50 | 120 | 1 |
| | Initial denaturation | 89 | 60 | |
| Stage 2 | Denaturation | 89 | 10 | 40 |
| | Annealing | 65 | 30 | |
| | Detection time | Delay | 5 | |
| | | Measure | 23 | |
| Melting | Start temperature | | 60° C. | |
| | Stop temperature | | 90° C. | |
| | Ramping rate | | 0.1° C./sec | |
| | Heating rate | | 10° C./sec | |
| | Cooling rate | | 5° C./sec | |

Figure 13A:
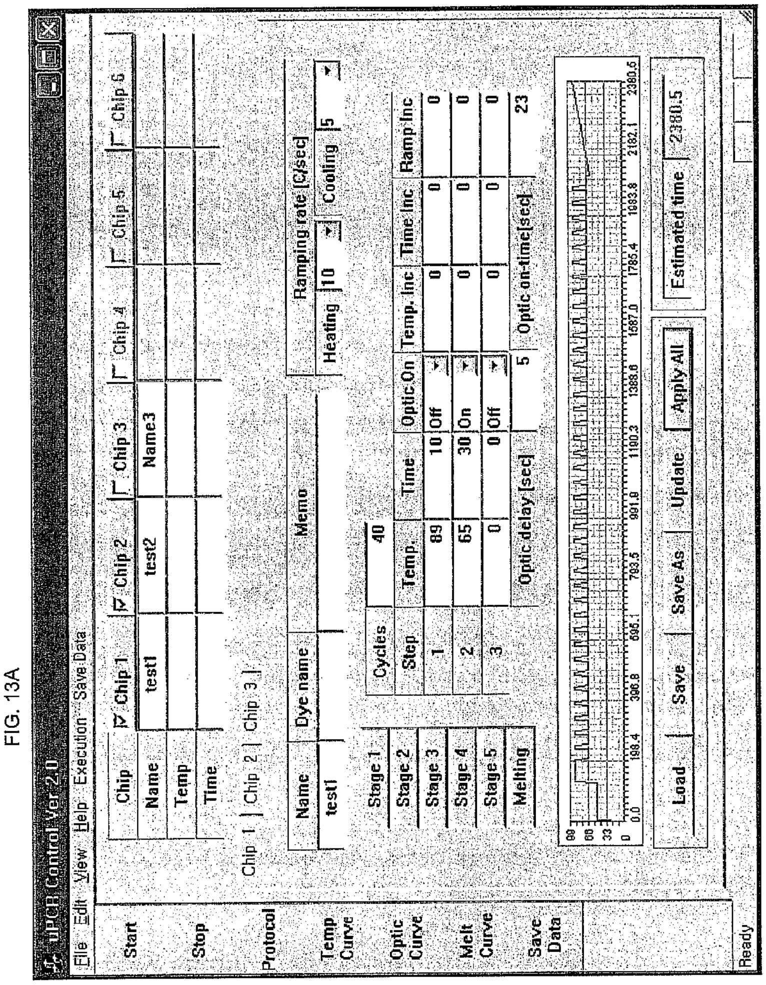
FIG. 13A is a view that illustrates real-time temperature profiles displayed on a screen of a real-time PCR monitoring apparatus, according to an embodiment of the present invention.

First, 1 μl of the PCR solution of Example 1 was loaded in each of micro PCR chips via a sample inlet as shown in FIGS. 4 and 5. The micro PCR chips were received in modules and then thermal cycling for the micro PCR chips were performed according to the PCR conditions presented in Table 2 like in FIG. 13A.

Figure 13B:
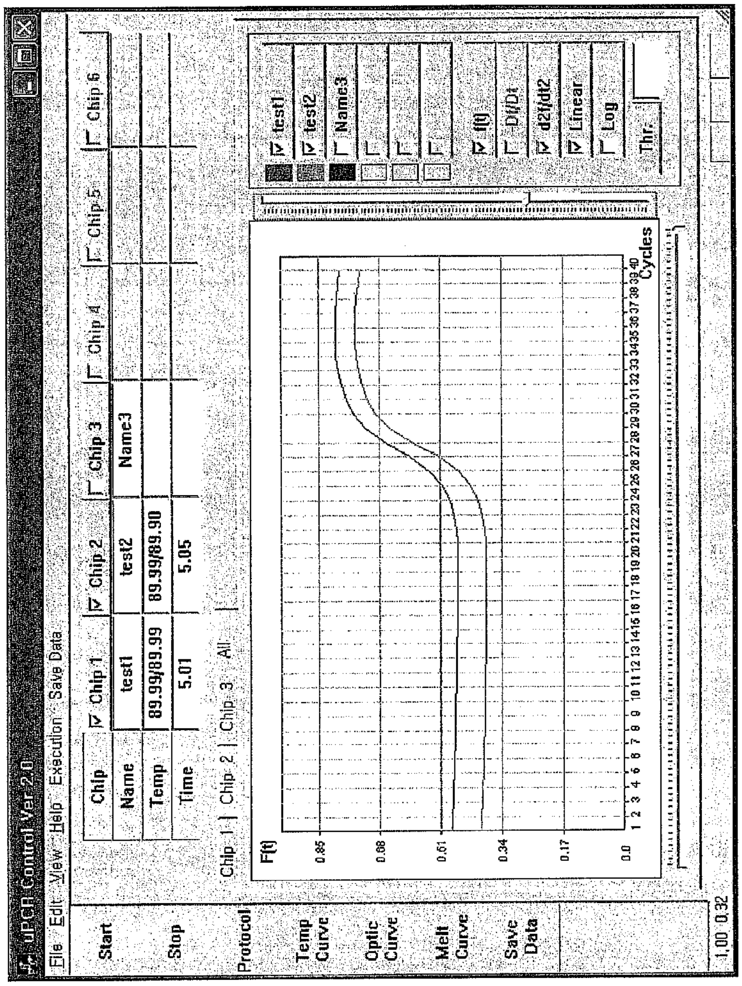
FIG. 13B is a view that illustrates real-time S-curves displayed on a screen of a real-time PCR monitoring apparatus, according to an embodiment of the present invention.

FIG. 13B is a graph that illustrates real-time signal values measured for 23 seconds during annealing with respect to the number of PCR cycles. As seen from the graph, the amounts of PCR products exponentially increased with time and signal values increased from after about 25 cycles. That is, the graph with a S-shaped curve appears.

Figure 13C:
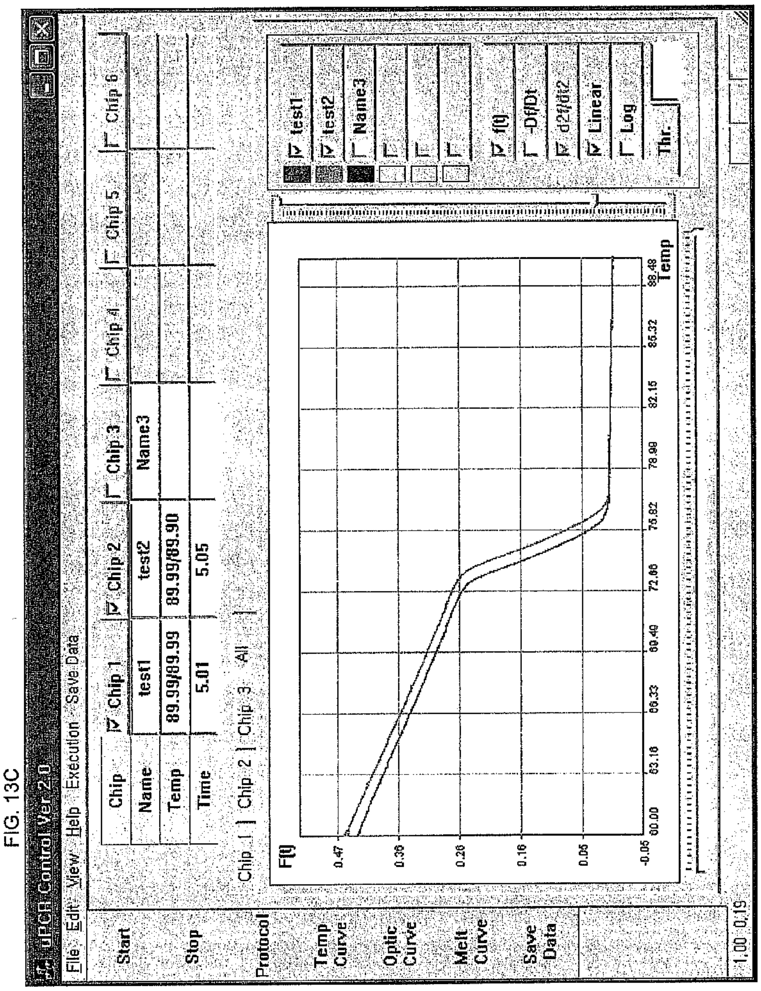
FIG. 13C is a view that illustrates real-time melting curves displayed on a screen of a real-time PCR monitoring apparatus, according to an embodiment of the present invention.

FIG. 13C shows reduction of fluorescence signals due to separation of double-stranded DNAs into single-stranded DNAs with increasing temperature. Based on analysis of these fluorescence signal patterns, information about the melting temperatures of DNAs may be obtained. Creation of the melting curves of DNAs enables identification of desired DNAs after amplification.

As described above, a multiple PCR system according to one or more embodiments of the present invention includes a plurality of PCR modules, each of which includes a microchip-type PCR tube having a PCR solution-containing PCR chamber, a heater, a detection unit that detects a PCR product signal based on the amount of a PCR product in the PCR solution, and a computing unit that adjusts the temperature of the PCR chamber of the PCR tube; and a host computer electrically connected to the modules. The computing unit of each PCR module independently controls the detection unit and the temperature of the PCR chamber of the PCR tube received in each PCR module. Therefore, PCR for different samples may be carried out at different temperature conditions at the same time and may be monitored in real time.

As described above, according to the one or more of the above embodiments of the present invention, in a PCR module, a multiple PCR system using the same, and a PCR monitoring method, co-amplification of different samples at different temperature conditions may be carried out and monitored in real time Furthermore, PCR may be performed for smaller amounts of unconcentrated samples at an enhanced temperature transition rate using a microchip-type PCR tube made of silicon with excellent conductivity.

What is claimed is:

1. A polymerase chain reaction (PCR) module comprising:

a heater comprising a heater wire and a temperature sensor;

a first housing comprising a lower base, and a clamp which is detachably disposed with the lower base and in which the heater is inserted such that the heater is fixed to the first housing;

a PCR tube comprising a surface which thermally contacts with the heater and a PCR chamber containing a PCR solution;

a second housing comprising a cover and an upper base detachably disposed with each other, and between which the PCR tube is fixed; and a detection unit which detects a PCR product signal, wherein the upper base exposes the surface of the PCR tube to outside the second housing, when the PCR tube is fixed in the second housing, the surface of the PCR tube thermally contacts the heater when the first housing is engaged with the second housing, the PCR tube is detachably disposed with the first and second housings; and the heater is detachably disposed with the first and second housings.

2. The PCR module of claim 1, further comprising a cooler lowering a temperature of the PCR tube.

3. The PCR module of claim 1, further comprising a heat-transfer facilitating layer interposed between the PCR tube and the heater.

4. The PCR module of claim 3, wherein the heat-transfer facilitating layer comprises a graphite sheet.

5. The PCR module of claim 1, further comprising a sealing member positioned on the second housing, and corresponding to an entrance of the PCR tube.

6. The PCR module of claim 1, wherein the PCR tube is of a microchip type and is made of silicon.

7. The PCR module of claim 1, wherein the heater is separately disposed from the PCR tube, and an upper surface of the heater contacts with a lower surface of the PCR tube to apply heat to the PCR tube.

8. The PCR module of claim 1, further comprising a computing unit for controlling PCR.

9. The PCR module of claim 1, wherein the detection unit is a fluorescence detector and the PCR product signal is a fluorescence signal, and the fluorescence detector detects the fluorescence signal.

10. The PCR module of claim 8, wherein the computing unit independently controls in real time the heater, the PCR tube, and the detection unit.

11. The PCR module of claim 8, wherein the computing unit controls in real time a temperature of the PCR solution in the PCR chamber disposed in the PCR tube.

12. A multiple PCR system comprising:

one or more PCR modules of claim 1; and a host computer controlling the PCR modules, wherein the PCR modules and the host computer are electrically connected through a wire or wireless mode.

13. The multiple PCR system of claim 12, wherein the host computer independently controls in real time the heater, the PCR tube, and the detection unit.

14. The multiple PCR system of claim 12, wherein the host computer controls in real time a temperature of the PCR solution in the PCR chamber disposed in the PCR tube.

15. The multiple PCR system of claim 12, wherein the detection unit in each PCR module detects the PCR product signal in the PCR tube and transmits the detected signal to the host computer through the wire or wireless mode.

16. The multiple PCR system of claim 15, wherein the PCR product signal is a fluorescence signal emitted from the PCR chamber in the PCR tube and the detection unit is a fluorescence detector that detects the fluorescence signal.

17. The multiple PCR system of claim 12, wherein the detection unit comprises a sensor detecting an electrical signal and the sensor detects the PCR product signal emitted from the PCR solution when an alternating current is applied to the PCR solution in the PCR chamber disposed in the PCR tube.

18. A multiple PCR system comprising:

one or more PCR modules of claim 1; and a host computer controlling the PCR modules, wherein the computing unit of each PCR module and the host computer are electrically connected through a wire or wireless network.

19. A real-time PCR monitoring method comprising:

(a) loading a PCR solution in a PCR chamber of a PCR tube received in each of one or more PCR modules of claim 1;

(b) performing PCR independently in the PCR chamber of the PCR tube of each PCR module having an independently determined temperature condition;

(c) detecting a PCR product signal based on the PCR performed in each PCR module; and (d) displaying data about the PCR product signal of each PCR module.

20. The real-time PCR monitoring method of claim 19, wherein the PCR product signal is a fluorescence signal emitted from the PCR chamber.

* * * * *